(12) United States Patent
Malik et al.

(10) Patent No.: US 8,123,799 B1
(45) Date of Patent: Feb. 28, 2012

(54) MODIFIED IMPLANTABLE DEVICE SURFACE AND A METHOD OF MAKING THE SAME

(75) Inventors: Shamim M. Malik, Temecula, CA (US);
Charles D. Claude, San Jose, CA (US);
Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 505 days.

(21) Appl. No.: 09/997,449

(22) Filed: Nov. 30, 2001

(51) Int. Cl.
*A61F 2/06* (2006.01)
(52) U.S. Cl. ..................................... 623/1.46
(58) Field of Classification Search ........ 623/1.42–1.46, 623/1.39, 1.4, 1.15, 1.13; 427/2.24–2.25, 427/2.3, 577, 525, 530; 209/192.16
See application file for complete search history.

(56) References Cited

U.S. PATENT DOCUMENTS 4,486,247 A * 12/1984 Ecer et al. ..................... 148/318
(Continued)

FOREIGN PATENT DOCUMENTS

| DE | 19855786 | | 6/2000 |
| DE | 19855786 A1 | * | 6/2000 |
| JP | 11-313884 | * | 11/1999 |

OTHER PUBLICATIONS

H. Yasuda et al., *Effect of Orientation and Mobility of Polymer Molecules at Surfaces on Contact Angle and Its Hysteresis*, J. Polymer Sci. 19:1285-1291 (1981).

(Continued)

*Primary Examiner* — Melanie Tyson
(74) *Attorney, Agent, or Firm* — Squire Sanders (US) LLP

(57) ABSTRACT

A medical device, such as a stent, is disclosed having a modified surface. A method of making the modification is also disclosed. The modification includes depositing a substance within the surface of the device and forming a film layer on the surface of the device. The substance can include carbon and the film layer can be a polymeric layer, such as a plasma polymerized organic film layer.

9 Claims, 2 Drawing Sheets

U.S. PATENT DOCUMENTS

| | | | |
|---|---|---|---|
| 5,040,548 A | | 8/1991 | Yock |
| 5,047,050 A | | 9/1991 | Arpesani |
| 5,049,132 A | | 9/1991 | Shaffer et al. |
| 5,084,151 A | * | 1/1992 | Vallana et al. ............ 204/192.11 |
| 5,165,919 A | | 11/1992 | Sasaki et al. |
| 5,188,734 A | | 2/1993 | Zepf |
| 5,192,311 A | | 3/1993 | King et al. |
| 5,336,518 A | * | 8/1994 | Narayanan et al. ............ 427/470 |
| 5,415,704 A | * | 5/1995 | Davidson ...................... 148/316 |
| 5,925,552 A | * | 7/1999 | Keogh et al. ................... 435/174 |
| 6,083,257 A | * | 7/2000 | Taylor et al. ................. 623/1.46 |
| 6,273,908 B1 | * | 8/2001 | Ndondo-Lay ................. 623/1.43 |
| 6,273,913 B1 | * | 8/2001 | Wright et al. ................ 623/1.42 |
| 6,335,029 B1 | * | 1/2002 | Kamath et al. ................ 424/423 |
| 6,613,432 B2 | * | 9/2003 | Zamora et al. ................ 428/409 |
| 6,712,846 B1 | * | 3/2004 | Kraus et al. .................. 623/1.46 |
| 7,056,523 B1 | | 6/2006 | Michal et al. |
| 7,077,860 B2 | | 7/2006 | Yan et al. |
| 7,163,165 B2 | | 1/2007 | Paul et al. |
| 7,163,715 B1 | | 1/2007 | Kramer |
| 7,201,940 B1 | | 4/2007 | Kramer |
| 7,396,582 B2 | | 7/2008 | Claude et al. |
| 7,441,513 B1 | | 10/2008 | Malik et al. |
| 2006/0178738 A1 | | 8/2006 | Yan et al. |
| 2007/0036905 A1 | | 2/2007 | Kramer |
| 2007/0166496 A1 | | 7/2007 | Kramer |

OTHER PUBLICATIONS

U.S. Appl. No. 09/977,449, filed Nov. 30, 2001, Malik et al.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).

Malik et al., *Overview of plasma source ion implantation research at University of Wisconsin-Madison*, J. Vac. Sci. Technol. B, No. 12, vol. 2, pp. 843-849 (Mar./Apr. 1994).

Malik et al., *Sheath dynamics and dose analysis for planar targets in plasma source ion implantation*, Plasma Sources Sci. Technol. vol. 2, pp. 81-85 (1993).

Scheuer et al., *Model of plasma source ion implantation in planar, cylindrical, and spherical geometries*, J. Appl. Phys., vol. 67, No. 3, pp. 1241-1245 (Feb. 1990).

Shamim et al., *Measurement of electron emission due to energetic ion bombardment in plasma source ion implantation*, J. Appl. Phys., vol. 70, No. 9, pp. 4756-4759 (Nov. 1991).

Shamim et al., *Measurements of Spatial and Temporal Sheath Evolution for Spherical and Cylindrical Geometries in Plasma Source Ion Implantation*, J. Appl. Phys., vol. 69, No. 5, pp. 2904-2908 (Mar. 1991).

U.S. Appl. No. 09/997,450, filed Nov. 30, 2001, Malik et al.

* cited by examiner

MODIFIED IMPLANTABLE DEVICE SURFACE AND A METHOD OF MAKING THE SAME

BACKGROUND OF THE INVENTION

1. Field of the Invention

This invention relates to implantable medical devices such as stents. More particularly, this invention relates to modifications made to the surface of the device for providing a platform for attachment of biocompatible materials or a coating, such as a polymeric coating used for the delivery of a therapeutic substance.

2. Description of the Background

Stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Mechanical intervention via stents has reduced the rate of restenosis; restenosis, however, is still a significant clinical problem. Accordingly, stents have been modified to function not only as mechanical scaffolding, but also to provide biological therapy.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

A common method of medicating a stent is by depositing a polymeric coating, impregnated with a therapeutic substance, on the surface of the stent. A polymer dissolved in a solvent is applied to the stent. A therapeutic substance can be dissolved or dispersed in the composition. The solvent is allowed to evaporate to form the coating. The application of the composition can be performed by spraying the composition on the stent or immersing the stent in the composition.

Various factors can lead to delamination of the polymeric coating from the surface of the stent. One example of such a factor includes mechanical stress caused by the radial expansion of the stent body. Additionally, polymeric materials have a tendency to adhere poorly to metallic materials, such as stainless steel, from which a stent is made. The embodiments of the present invention address such deficiencies by providing a modified stent surface and methods of forming a coating on the stent surface.

SUMMARY

In accordance with on aspect of the invention, a medical device, such as a stent, having a modified surface is provided. The device includes a substance implanted in at least a region of the surface and a film layer deposited on the region having the implanted substance. The substance can include carbon. The film layer can include an organic or plasma polymerized polymeric layer. The device can also include a polymeric coating containing a therapeutic substance deposited on the film layer.

In accordance with another aspect of the invention, a method of modifying a surface of an implantable device, such as a stent, is provided comprising implanting a substance, such as carbon, at a depth within the surface of the device. The method can additionally comprise depositing a polymeric film layer on the surface of the stent, the polymeric film layer being a plasma polymerized film layer. The method can additionally comprise forming a polymeric coating containing a therapeutic substance on the plasma polymerized film layer.

In accordance with one embodiment, carbon can be implanted by sputtering carbon off a grid and onto the surface of the device. Alternatively, carbon can be deposited by introducing a carbon-based gas, such as methane, into a chamber and initiating a plasma.

In accordance with one embodiment, the film layer can be deposited by introducing acrylic acid into a reaction chamber and initiating a plasma to form an acrylate or acrylate-like film layer. Carbon dioxide can also be introduced into the chamber to limit the rate of de-carboxylation of the acrylic acid.

DETAILED DESCRIPTION

A medical device is broadly intended to include any device for being inserted permanently or temporarily, for being used for the release of an active agent, for upholding luminal patency, or for any other treatment purpose in a human or veterinary patient. Examples of such devices include self-expandable stents, balloon-expandable stents, stent grafts, grafts (e.g., aortic grafts), artificial heart valves, cereboral fluid shunts, pacemaker electrodes, axius coronary shunts, and endocardial leads (e.g., FINELINE™ and ENDOTAK™, available from Guidant Corporation). The underlying structure of the device can be of virtually any design, and the particular configuration of the device is not of critical importance to the practice of the present invention. The device can be made of a metallic material, such as stainless steel, or an alloy.

Figure 1:
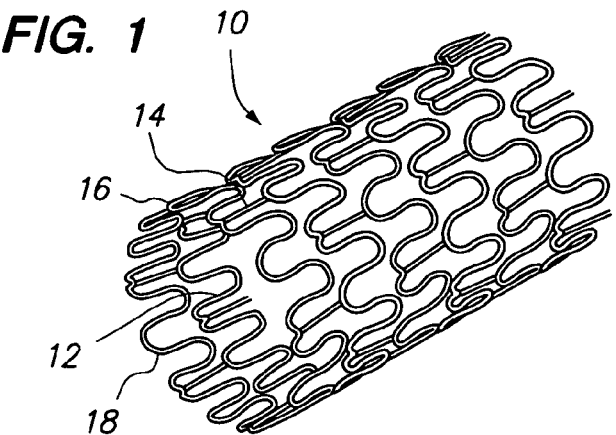
FIG. 1 illustrates a conventional stent.
Figure 2A:
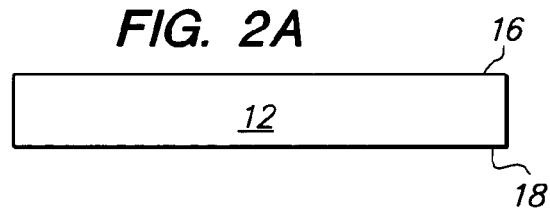
FIGS. 2A-2D illustrate various embodiments of the process of the invention.

The present invention will be described with reference to a vascular stent. FIG. 1 illustrates one example of a conventional stent 10, the structure of which includes struts 12 connected by elements 14. Struts 12 and elements 14 define a tubular body having an outer or tissue contacting surface 16 and an inner surface 18. FIG. 2A illustrates a section of one of struts 12 as will be modified as described hereinafter. It is understood that any portion of outer surface 16, including selected areas of elements 14 can be similarly treated and that the modification is not limited to any particular region of outer surface 16 of stent 10.

Figure 2B:
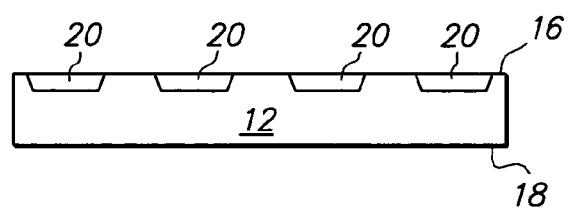

FIG. 2B illustrates amorphous carbon deposits 20 implanted in outer surface 16 at a selected depth of, for example, not more than about 2000 angstroms. A variety of techniques may be employed for the implantation of carbon in outer surface 16. Prior to the implantation of carbon, outer surface 16 can be cleaned by, for example, exposure of stent 10 to argon plasma or any other suitable cleaning method so as to rid stent 10 surfaces of contaminants that are introduced during the manufacturing process.

Figure 3:
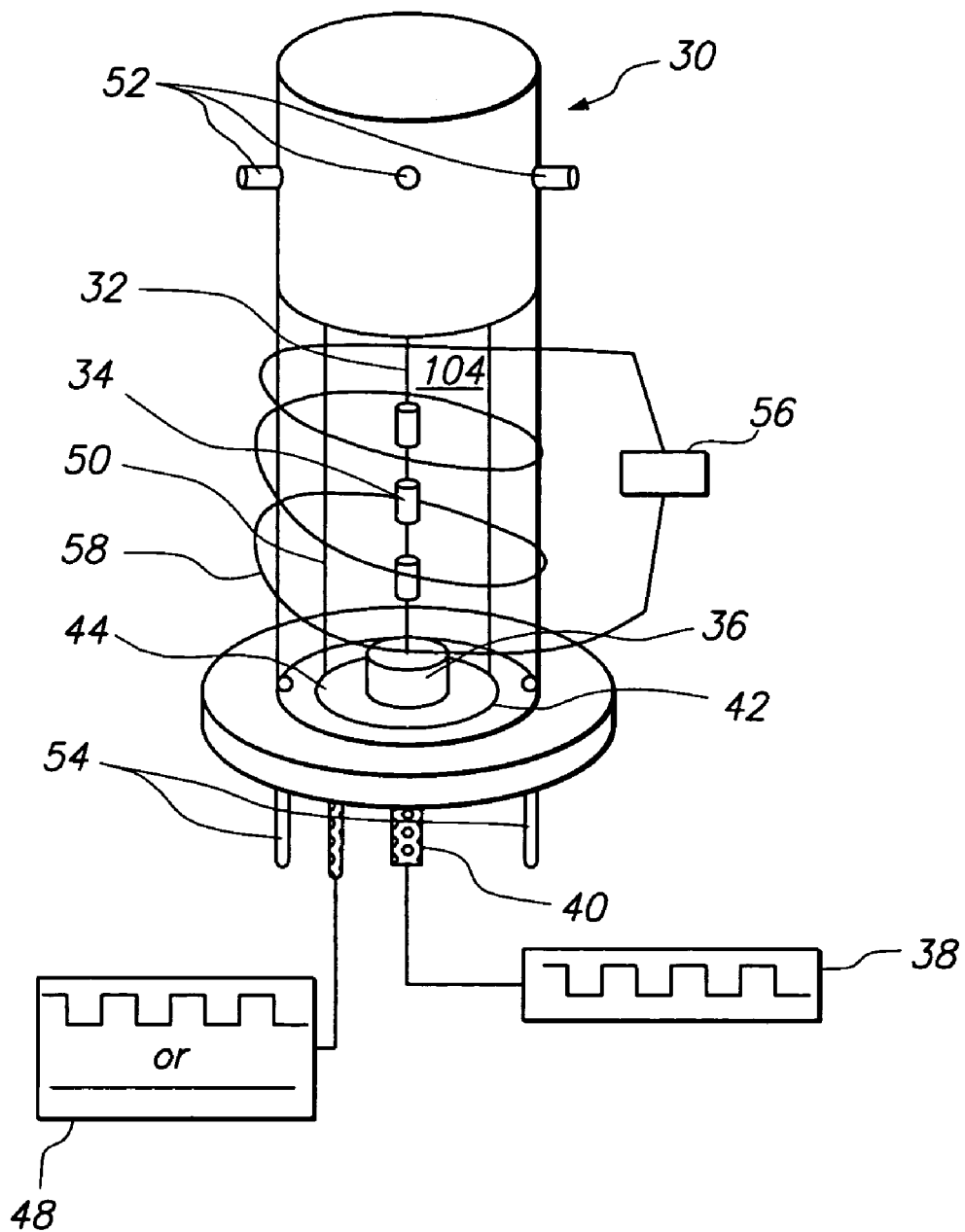
FIG. 3 schematically illustrates one embodiment of a reaction chamber that can be employed for the practice of the present invention.

In accordance with one method, stent 10 is placed on mandrel and is positioned within a reaction chamber in any suitable orientation. One example of a suitable system for carrying out the process is illustrated in FIG. 3, the details of which are described later in the specification.

A sputtering grid is positioned in the chamber and is in conformity with stent 10 so as to allow ions to bombard stent 10 equally from all directions. A gaseous medium such as argon is introduced into the chamber to be converted into ionized plasma. The medium can also include other components in addition to argon such as nitrogen (e.g., 1:1 v/v). An RF energy source is used to generate plasma for sputtering carbon from the grid and onto surface 16 of stent 10. Process parameters that can be employed are listed in Table 1 below:

TABLE 1

| Process | Parameter Range | Exemplary Value |
|---|---|---|
| argon | — | >99.9% by volume |
| gas flow rate (sccm) | 10 to 500 | 50 |
| volume of chamber (cm$^3$) | — | 2000 |
| pressure (mTorr) | 0.1 to 500 | 50 |
| RF power (watts) | 10 to 1000 | 200 |
| RF frequency (MHz) | 2 to 2800 | 13.56 |
| bias voltage-stent (KV) | −5 to −30 | −10 |
| pulse width-stent (microseconds) | 5 to 20 | 20 |
| frequency-stent (Hz) | DC-2000 | 500 |
| bias voltage-grid (V) | −300 to −5000 | −1000 |

In lieu of using a carbon-based grid, in accordance with another embodiment, a carbon-based gas such as methane can be introduced into the chamber and a plasma initiated. High voltage pulses are applied to stent 10 to deposit the ions in surface 16. The wall of the chamber can be grounded. Table 2 is the list of process parameters which can be employed:

TABLE 2

| Process | Parameter Range | Exemplary Value |
|---|---|---|
| methane | — | >99.9% by volume |
| gas flow rate (sccm) | 10 to 200 | 30 |
| pressure (mTorr) | 0.1 to 2 | 0.5 |
| RF power (watts) | 10 to 1000 | 100 |
| RF frequency (MHz) | 2 to 2800 | 13.56 |
| bias voltage-stent (KV) | −10 to −80 | −50 |
| frequency-stent (Hz) | DC to 2000 | 200 Hz |
| pulse width (microseconds) | 5 to 100 | 20 |

A carbon deposit in the surface of the stent provides a site from which covalent bonds can be formed with a plasma deposited polymer film layer.

Subsequent to the implantation of the carbon deposit, the reaction chamber can be pumped down and stent 10 can be re-exposed to argon plasma for cleaning stent 10. The cleaning process can be performed under the following parameters:

TABLE 3

| Process | Parameter Range | Exemplary Value |
|---|---|---|
| argon | — | >99.9% by volume |
| gas flow rate (sccm) | 10 to 250 | 250 |
| pressure (mTorr) | 10 to 250 | 230 |
| RF power (W) | 50 to 450 | 400 |
| RF frequency (MHz) | 2 to 2800 | 13.54 |
| Time (minutes) | 3 to 30 | 5 |

Figure 2C:
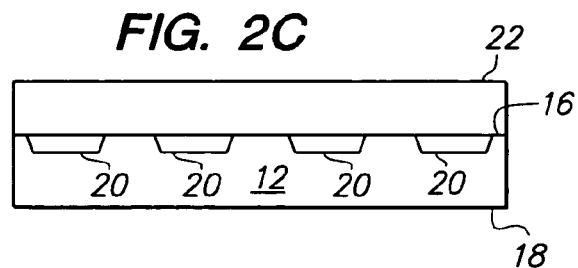

A film layer 22, as illustrated in FIG. 2C can then be deposited on outer surface 16 of stent 10 by plasma polymerization, as is understood by one of ordinary skill in the art. In one embodiment, the film layer provides a carboxylic acid-rich organic surface. However, a variety of other functionalities, include amine or sulfate functionalities, can be plasma polymerized on outer surface 16 of stent 10. Masking techniques can also be employed to strategically deposit the plasma polymerized film layer 22 on designated areas of surface 16 of stent 10.

The plasma-polymerized film layer 22 can include an acrylate or acrylate-like polymer layer deposited onto carbon deposits 20 by exposing stent 10 to an acrylic acid plasma. One having ordinary skill in the art will recognize that some fragmentation of the acrylate typically occurs during the plasma polymerization deposition of film layer 22, resulting in an acrylate-like polymer layer of fragmented acrylate, which will be covalently bonded to carbon deposits 20. Acrylic acid can be used as the source gas for generating the plasma. Table 4 is a list of process parameters which can be used for the deposition of the plasma polymerized film layer 22:

TABLE 4

| Process | Parameter Range | Exemplary Value |
|---|---|---|
| carbon dioxide flow rate (sccm) | 60 to 200 | 90 |
| acrylic acid flow rate (ml/min) | 0.05 to 0.35 | 0.2 |
| pressure (mTorr) | 70 to 250 | 150 |
| RF power (W) | 50 to 250 | 100 |
| RF frequency (MHz) | 2 to 2800 | 13.54 |
| power/flow rate (MJ/Kg) | 9 to 35 | 13.7 |

The acrylic acid plasma can be applied for about 10 minutes, the time limit being dependent on the desired thickness of film layer 22. The thickness of film layer 22 can be about 20 nm to about 500 nm, more narrowly about 70 nm to about 150 nm. For example, the thickness can be about 125 nm. As indicated by Table 4, carbon dioxide can be also supplied with acrylic acid to limit the rate of de-carboxylation which can occur with an organic acid in a plasma field. In accordance with another embodiment, a pulsed plasma condition, as is understood by one of ordinary skilled in the art, can be employed for the deposition of film layer 22. The process parameters are similar to that of Table 4, but for the power range being between about 100 W to about 450 W, with a preferred plasma power of about 250 W to about 350 W. For the implementation of pulsed plasma, the RF power can be pulsed at about 500 to 4000 Hz using, for example, a square wave pulse sequence. Preferably, the RF power can be pulsed at about 1000 Hz to about 1250 Hz. The duty period, the time in which the power is on, can be between 15% and 100%, preferably between 20% and 35%. With the use of pulsed plasma condition, the rate of de-carboxylation can be further limited.

Following deposition of the plasma-polymerized film layer 22, the plasma field can be purged with argon without an applied RF field to allow surface free radicals to be recombined prior to exposure to atmospheric oxygen. Table 5 provides parameters for this quenching process:

TABLE 5

| Process | Parameter Range | Exemplary Value |
|---|---|---|
| argon | — | (>99.9% by volume) |
| gas flow rate (sccm) | 30 to 300 | 230 |
| Pressure (mTorr) | 50 to 500 | 250 |
| time (minutes) | 2 to 10 | 3 |

Figure 2D:
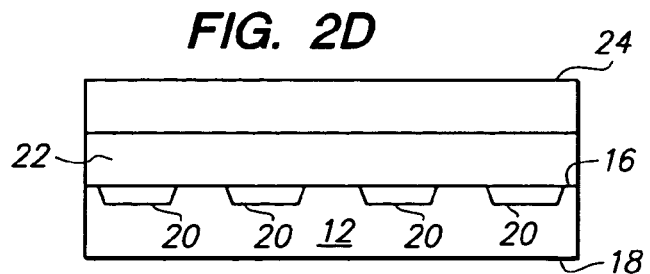

Plasma polymerized films deposited using acrylic acid produce films with a high density of carboxylic functional groups. The functional groups can be modified for the attachment of biocompatible or non-fouling components such as polyethylene glycol, heparin, heparin having hydrophobic counter ions, and superoxide dismutase mimic (SODm). Alternatively, as illustrated in FIG. 2D, a polymeric coating 24 can be deposited on film layer 22. Strong interaction via hydrogen bonding can be present between film layer 22 and polymeric coating 24. Polymeric coating 24 can be made from any suitable biocompatible polymer, such as ethylene vinyl alcohol copolymer or any other suitable polar material. A composition containing a polymer can be sprayed on film layer 22 or stent 10 can be immersed in the solution. The evaporation of a solvent used to dissolve the polymer results in the solidification of polymer coating 24.

Polymeric coating 24 can contain or be impregnated with a therapeutic substance. This can be achieved by adding the therapeutic substance to the composition prior to the spray or dip process. The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN® available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (bivalirudin, Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Example of the Reaction Chamber

The above-described methods can be performed by any suitable apparatus known to one of ordinary skill in the art. On example of such an apparatus is a plasma reaction chamber 30 illustrated in FIG. 3. Chamber 30 can be cylindrical in shape and can be fabricated from any number of suitable materials, such as, stainless steel, glass, and aluminum. By way of example, chamber 30 can be from about 4 inches (10.16 cm) to about 15 inches (38.1 cm) in diameter and from about 5 inches (12.7 cm) to about 18 inches (45.72 cm) in height.

A mandrel 32 holds a single medical device 34 (e.g., stent 10) or multiple medical devices 34 in position relative to the interior wall of chamber 30. Medical device 34 can be oriented at any position within chamber 30 as required to achieve a desired implantation or deposition. One end of mandrel 32 can be coupled to an electrode 36.

Electrode 36 can be made from of any suitable electrically conductive material including, but not limited to, steel, copper, chromium, nickel, wolfram, iron, and similar materials. A first power source 38, electrically coupled to electrode 36 via electrical feedthrough port 40, can apply a voltage to electrode 36.

In one embodiment, an insulator 42, formed of a non-electrically conductive material, including materials such as rubber, ceramic, or plastic is provided. Insulator 42 can include a connector 44, which can be either electrically coupled to first power source 38 or an independent second power source 48 for applying a voltage to a sputtering grid 50.

Sputtering grid 50 can be positioned within chamber 30 in symmetrical conformity about medical device 34 so as to allow equal bombardment of device 24 from all directions. Sputtering grid 50 can be manufactured from carbon or, alternatively, can be made of a base material that is coated with carbon. Sputtering grid 50 can be cylindrically shaped. Sputtering grid 50 can be of solid construction or perforated. By way of example, sputtering grid 50 can be a perforated cylinder measuring approximately 0.5 inches (1.27 cm) to 3.0 inches (7.62 cm) in diameter, approximately 2 inches (5.08 cm) to 12 inches (30.48 cm) in height, and approximately $\frac{1}{32}$ of an inch (0.08 cm) thick. The diameter of the perforations can be from about 0.125 inches (0.318 cm) to about 0.25 inches (0.635 cm). The percentage of the grid occupied by perforation, as opposed to carbon sputtering material, can be from about 40% to about 80% of the total surface area.

Gas ports 52 can be positioned on top of chamber 30, while aspiration ports 54 can positioned at or near the base of chamber 30. Gas ports 52 are used to flux a gaseous medium in liquid or vapor form into chamber 30, where it is converted into ionized plasma. Aspiration ports 54 are used after processing is complete, or when a new gas is desired, to purge chamber 30.

Additionally, an apparatus for accomplishing the method of the present invention includes a plasma-generating assembly. The plasma-generating assembly can be, for example, a radio frequency source and antenna, a microwave source, or any other suitable element known to one of ordinary skill in the art. By way of example, FIG. 3 illustrates a radio frequency source 56, such as that manufactured by Dressler of Germany, and an antenna 58. In one such embodiment, antenna 58 can be a radio-frequency conducting filament that is wrapped about chamber 30 in a helical or corkscrew-like fashion.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A stent comprising:
   a metallic stent body having a stent body surface;
   a molecular carbon deposit present at a depth of not more than about 2000 Å beneath the stent body surface; and
   a plasma-polymerized polymer film layer deposited over the stent body surface and in intimate contact with the stent body surface, wherein the plasma-polymerized film layer is chemically bonded to the carbon deposit.

2. The stent of claim 1, wherein the plasma-polymerized polymer film layer comprises an acrylate.

3. The stent of claim 1, wherein the plasma-polymerized polymer film layer is formed by exposing the stent to an acrylic acid plasma.

4. The stent of claim 1, wherein the plasma polymerized film layer comprises functional groups selected from the group consisting of carboxylate, amine and sulfate.

5. The stent of claim 1, wherein the surface of the stent is the tissue-contacting surface of the stent body.

6. The stent of claim 1, wherein the metallic stent body comprises stainless steel.

7. The stent of claim 1, further comprising a polymeric layer comprising a therapeutic substance formed on the plasma-polymerized polymer film layer.

8. The stent of claim 1, wherein the metallic stent body comprises a radially expandable tubular body.

9. The stent of claim 1, wherein the metallic stent body comprises an alloy.

* * * * *